US011696982B2

(12) United States Patent
Barnes et al.

(10) Patent No.: US 11,696,982 B2
(45) Date of Patent: Jul. 11, 2023

(54) ATTACHMENT SYSTEM FOR SECURING MEDICAL DEVICES TO SUPPORT STRUCTURES

(71) Applicant: DeRoyal Industries, Inc., Powell, TN (US)

(72) Inventors: Scott Douglas Barnes, Knoxville, TN (US); Vincent Denis Jardret, Powell, TN (US); Dhanvin Sunil Desai, Knoxville, TN (US); Breanna Julia Rhyne, Powell, TN (US); Joe Lowell Smith, Powell, TN (US); Walter Cleveland Cowart, Blaine, TN (US)

(73) Assignee: DeRoyal Industries, Inc., Powell, TN (US)

( * ) Notice: Subject to any disclaimer, the term of this patent is extended or adjusted under 35 U.S.C. 154(b) by 172 days.

(21) Appl. No.: 17/193,551

(22) Filed: Mar. 5, 2021

(65) Prior Publication Data
US 2021/0275739 A1    Sep. 9, 2021

Related U.S. Application Data

(60) Provisional application No. 62/985,349, filed on Mar. 5, 2020.

(51) Int. Cl.
*A61M 5/14*    (2006.01)

(52) U.S. Cl.
CPC ..... *A61M 5/1415* (2013.01); *A61M 2209/082* (2013.01)

(58) Field of Classification Search
CPC .......... A61M 5/1415; A61M 2209/082; A61M 5/1413; A61M 5/1414; A61M 5/1417; A61B 90/57; A61G 7/0503

USPC ......... 211/85.13; 248/218.4, 229.12, 229.13, 248/229.14, 230.1–230.7
See application file for complete search history.

(56) References Cited

U.S. PATENT DOCUMENTS

| | | | | | |
|---|---|---|---|---|---|
| 3,734,439 | A | * | 5/1973 | Wintz | A47G 23/0241 248/230.8 |
| 3,888,354 | A | * | 6/1975 | Margolin | A47F 5/13 211/110 |
| 3,915,189 | A | * | 10/1975 | Holbrook | A61M 1/60 248/223.41 |
| 4,131,259 | A | * | 12/1978 | Franks | A47G 7/044 D6/535 |
| 4,858,869 | A | * | 8/1989 | Stang | A47G 23/0225 248/314 |
| 5,026,016 | A | * | 6/1991 | Lisowski | F16B 21/09 248/314 |

(Continued)

OTHER PUBLICATIONS

International Search Report and Written Opinion for PCT/US2021/021132, dated May 20, 2021, 19 pages.

*Primary Examiner* — Ingrid M Weinhold
(74) *Attorney, Agent, or Firm* — Luedeka Neely Group, P.C.

(57) ABSTRACT

A medical device attachment system including a mounting system having a receptacle for receiving a hook attached to a medical device. The receptacle includes a rear wall, a first side wall, a second side wall, and a notch formed by the walls for closely receiving the hook. A plate mount forms a front wall of the receptacle and an appropriate attachment component is secured to the mounting plate for removably securing the mounting system to a desired support structure for the medical device.

18 Claims, 5 Drawing Sheets

(56) References Cited

U.S. PATENT DOCUMENTS

| | | | | |
|---|---|---|---|---|
| 5,356,105 | A | * | 10/1994 | Andrews .................. B63B 35/14 |
| | | | | 248/221.11 |
| 5,829,723 | A | | 11/1998 | Brunner et al. |
| 6,390,427 | B1 | * | 5/2002 | McConnell ............ B60N 3/107 |
| | | | | 248/228.3 |
| 6,409,131 | B1 | * | 6/2002 | Bentley ............... A61M 5/1415 |
| | | | | 248/230.1 |
| 6,481,679 | B1 | | 11/2002 | Bennett et al. |
| 7,261,264 | B2 | * | 8/2007 | Moran .................. A01K 5/0114 |
| | | | | 248/221.11 |
| D567,740 | S | * | 4/2008 | Smith .......................... D12/411 |
| 7,533,854 | B2 | * | 5/2009 | Aube .................. A61M 5/1417 |
| | | | | 248/95 |
| 7,624,901 | B1 | * | 12/2009 | Mozes ...................... A45F 5/02 |
| | | | | 206/37 |
| 8,011,071 | B2 | * | 9/2011 | O'Brien ............ A61M 16/1075 |
| | | | | 248/221.11 |
| 8,695,957 | B2 | * | 4/2014 | Quintania ............... B25B 5/006 |
| | | | | 269/74 |
| 8,807,514 | B1 | * | 8/2014 | Giauque ................ A01K 39/02 |
| | | | | 248/156 |
| 9,121,423 | B2 | * | 9/2015 | Sharpe ................. F16M 13/022 |
| 9,999,719 | B2 | * | 6/2018 | Kitchen .............. A61M 5/1415 |
| 10,959,895 | B2 | * | 3/2021 | Jepsen ................... A61B 50/28 |
| 11,071,384 | B2 | * | 7/2021 | Blewett ................ A47B 96/066 |
| 2009/0294604 | A1 | * | 12/2009 | Sunderland ............ F16M 11/42 |
| | | | | 248/227.3 |
| 2009/0301927 | A1 | | 12/2009 | Fvlbrook et al. |
| 2011/0084181 | A1 | * | 4/2011 | Bowers ................ A61G 7/0503 |
| | | | | 248/95 |
| 2011/0101587 | A1 | | 5/2011 | Quintania et al. |
| 2014/0231605 | A1 | | 8/2014 | Sharpe et al. |

* cited by examiner

ATTACHMENT SYSTEM FOR SECURING MEDICAL DEVICES TO SUPPORT STRUCTURES

CROSS REFERENCE TO RELATED APPLICATIONS

This application claims priority to U.S. Provisional Application Ser. No. 62/985,349 filed Mar. 5, 2020, entitled "Medical Device Attachment System for IV Poles & Bed Rails," the entire contents of which is incorporated herein by reference.

FIELD

This disclosure relates to the field of portable medical device attachment systems. More particularly, this disclosure relates to an attachment system for connecting a portable medical device to a pole structure such as an IV pole or bed rail.

BACKGROUND

Some portable medical devices with patient connections need to attach to an IV pole or to bed rails such that the medical devices can operate from a safe location while the patient is lying in a hospital bed. Many portable medical devices also need to be able to move with the patient around a room or in a hallway when the patient is not lying on the hospital bed. Medical staff often times have to handle these medical devices while also helping their patients get out of bed or move as needed.

For example, negative pressure wound therapy (NPWT) units include tubing from the unit to a wound dressing connected to the patient. During treatment, the NPWT units should be securely attached to a bedrail while the patient is in the bed. When the patient moves within the room or into the hallway, the medical staff should be able to easily move the NPWT device from the bedrail to an IV pole, wheelchair, etc. Whether the patient is lying in bed or moving about, the device should be held securely to enable a number of functions such as connecting and disconnecting a canister from the pump device, interacting with inputs on the user interface of the unit, reading a fluid level within the canister, etc.

Prior attachment systems require the use of screws, springs, extended protrusions, etc. that make the change from attachment from one location (e.g., bed rail) to another location (e.g., IV pole) difficult and time consuming. In particular, prior attachment systems typically require a two-handed operation when removing or securing a portable medical device to a particular location.

What is needed therefore is an attachment system that provides a quick, one-handed, secure attachment of medical devices to an IV pole or bed/chair rail.

SUMMARY

The above and other needs are met by a medical device attachment system including a hook including a top portion and a shank configured to extend down from the top portion of the hook and a receptacle including a rear wall, a first side wall, a second side wall, and an opening formed by the rear wall, the first side wall, and the second side wall, the opening including at least a lower notch dimensioned and configured for closely receiving an end portion of the shank of the hook. The attachment system further includes a mounting system including a plate mount having a first side and a second side and an attachment component configured to be secured to the second side of the mounting plate for removably securing the mounting system to a desired support structure for the medical device. One of the hook and the receptacle is configured to be attached to the exterior surface of the medical device and one of the hook and the receptacle is configured to be attached to the first side of the plate mount such that the medical device is removably secured to the desired support structure when the end portion of the shank of the hook is inserted into lower notch of the receptacle.

According to certain embodiments, the receptacle further includes an upper notch formed in a top surface of the rear wall, the upper notch being vertically aligned with the lower notch and dimensioned and configured for receiving the top portion of the hook. In some embodiments, at least a portion of the top surface of the rear wall is sloped downward towards the upper notch.

According to certain embodiments, at least one of the first side wall and the second side wall include a sloped portion that is sloped downwards towards the lower notch.

According to certain embodiments, the first side wall and the second side wall each include a sloped portion that is sloped downwards towards opposing sides of the lower notch.

According to certain embodiments, the first side of the plate mount is configured to be removably attached to one of the receptacle and the hook such that the plate mount can be removed and rotated for rotating the attachment component secured to the mounting plate.

According to certain embodiments, when the hook is attached to the first side of the plate mount, the plate mount and the hook are formed as a unitary component and, when the receptacle is attached to the first side of the plate mount, the plate mount and the receptacle are formed as a unitary component.

According to certain embodiments, the plate mount is configured to receive differently configured attachment components for removably securing the mounting systems to differently configured support structures.

According to certain embodiments, the attachment component is a clamp device for removably securing the mounting system to a pole structure. In some embodiments, the clamp device is configured to be rotated with respect to the mounting plate such that the clamp device is configured to be removably secured to a vertical pole structure in a first orientation and removably secured to a horizontal pole structure in a second orientation.

According to certain embodiments, the medical device attachment system further includes a first mounting system for securing to a first desired support structure and a second mounting system for securing to a second desired support structure such that the medical device may be moved from between the first desired support structure and the second desired support structure without removing either of the first mounting system from the first desired support structure or the second mounting system from the second desired support structure.

According to certain embodiments, the medical device attachment system further includes a handle configured to be attached to the medical device, the handle including a width that is substantially the same as a width of a top portion of the opening of the receptacle.

According to certain embodiments, the rear wall of the receptacle includes a thickness slightly less than a depth of a space provided by the top portion of the hook.

According to another aspect of the disclosure, a method for removably attaching a medical device to a support structure is provided. The medical device includes a hook having a top portion configured to extend substantially perpendicular to an exterior surface of the medical device and a shank configured to extend down from the top portion of the hook such that a space is provided between the exterior surface of the medical device and the shank. The method includes securing a mounting system to the support structure with the mounting system including a receptacle having a rear wall, a first side wall, a second side wall, and an opening formed by the rear wall, the first side wall, and the second side wall. The opening includes at least a lower notch dimensioned and configured for closely receiving an end portion of the shank of the hook. The mounting system further includes a plate mount for forming a front wall of the receptacle and an attachment component secured to the mounting plate for securing the mounting system to the support structure. The method further includes positioning the hook of the medical device over the opening of the receptacle and lowering the shank of the hook into the opening such that the rear wall of the receptacle is disposed at least partially in the space between the exterior surface of the device and the shank of the hook and an end portion of the shank of the hook is inserted into the lower notch.

According to certain embodiments, at least one of the first side wall and the second side wall of the receptacle include a sloped portion that is sloped downwards towards the lower notch and the lowering step includes sliding the shank of the hook along the sloped portion until the end portion of the shank is inserted into the lower notch.

According to certain embodiments, the receptacle further includes an upper notch formed in a top surface of the rear wall that is vertically aligned with the lower notch and the lowering step includes lowering the shank of the hook until the top portion of the hook is inserted into the upper notch.

According to certain embodiments, the method further includes rotating the attachment component as compared to the receptacle based on the orientation of the support structure to which the mounting system is secured to during the securing step. In some embodiments, the attachment component is a clamp device for securing the mounting system to a pole structure and the orientation of the pole structure includes one of a substantially vertical orientation and a substantially horizontal orientation. In some embodiments, the rotating the attachment component includes one of rotating the plate mount with respect to the receptacle and rotating the attachment component with respect to the plate mount.

According to certain embodiments, the mounting system includes a first mounting system for securing to a first support structure and a second mounting system for securing to a second support structure, and the method further includes moving the medical device between the first and second support structures without removing the first mounting system from the first support structure and without removing the second mounting system from the second support structure.

BRIEF DESCRIPTION OF THE DRAWINGS

Other embodiments of the disclosure will become apparent by reference to the detailed description in conjunction with the figures, wherein elements are not to scale so as to more clearly show the details, wherein like reference numbers indicate like elements throughout the several views, and wherein.

DETAILED DESCRIPTION

Figure 4:
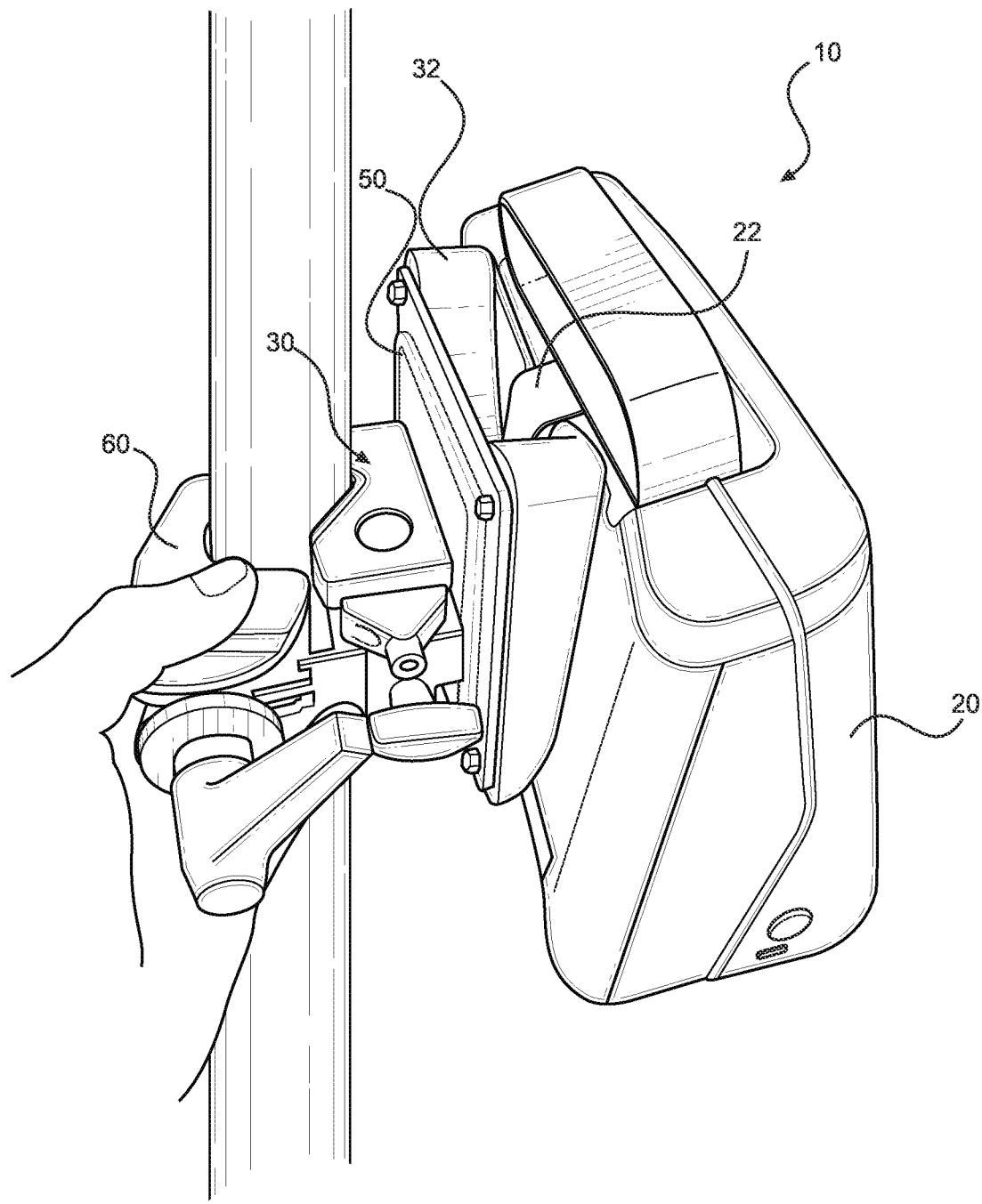
FIG. 4 depicts a side perspective view of the attachment system with the attachment component being in an orientation for securing a medical device to a vertical pole structure according to one embodiment of the disclosure.

Referring initially to FIG. 4, the present medical device attachment system 10 generally includes two parts: (1) a hook 22 extending downward preferably on the rear side of a medical device 20 (an exemplary medical device 20 is shown in the figures of the present application as a NPWT device with hook 22 attached thereto); (2) a mounting system 30 having a receptacle 32 for receiving the hook 22 of the medical device 20, a mounting plate 50, and an attachment component 60 for securing the receptacle 32 to a desired support structure (e.g., IV pole, bed/chair rail, etc.). In certain embodiments, multiple mounting systems 30 may be provided such that the medical device 20 is moved between two or more support structures without removing the mounting system 30 from the support structures during the transfer process. In this embodiment, only one hand should be needed to move the medical device 20 from one support structure to another support structure. In other embodiments, the mounting system 30 is removed from the first support structure and attached to a second support structure when it is desired to change the support structure in which the medical device is secured.

Figure 1:
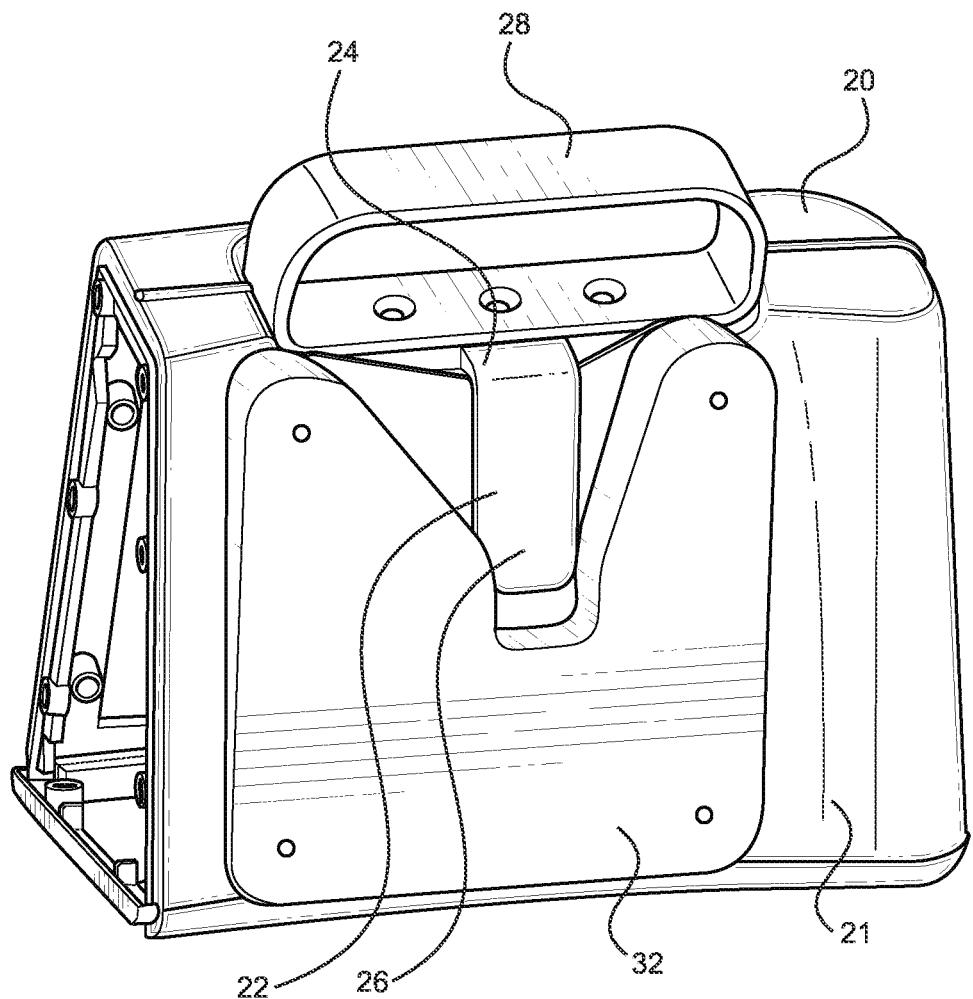
FIG. 1 depicts a rear perspective view an exemplary medical device with a hook attached thereto being inserted into a receptacle according to one embodiment of the present disclosure.

With reference to FIG. 1 (which depicts receptacle 32 receiving hook 22 with the mounting plate 50 and attachment component 60 of mounting system 30 omitted), hook 22 includes a top/bend portion 24 and shank 26. The top portion 24 is configured to extend substantially perpendicular to the rear surface 21 of the medical device 20 (or otherwise to the exterior surface if hook 22 is connected to a different portion of the medical device 20). The shank 26 is configured to extend down from the top portion 24 such that a space is provided between the rear surface 21 of the medical device 20 and the shank 26 of hook 22.

Figure 2:
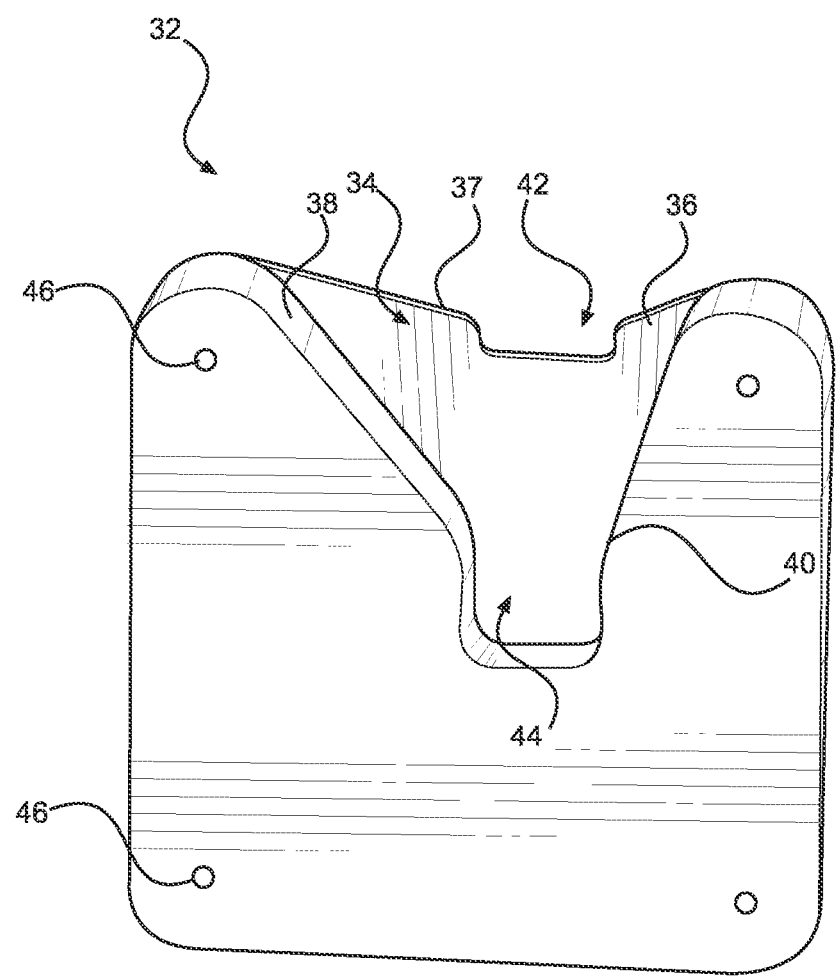
FIG. 2 depicts a front perspective view of a receptacle according to one embodiment of the present disclosure.

Referring to FIGS. 1 and 2, the receptacle 32 of mounting system 30 includes an opening 34 for receiving the hook 22 attached to the medical device 20. While it should be understood that the receptacle 32 and corresponding opening 34 may take various forms for receiving hook 22, the exemplary embodiment of the present disclosure includes a rear wall 36 intended to be positioned along the rear surface 21 of the medical device 20 (as depicted in FIG. 1), a first side wall 38, and a second side wall 40. The top surface 37 of the rear wall 36 includes an upper notch 42 disposed between the first side wall 38 and the second side wall 40 that is dimensioned and configured to correspond to the dimensions and configuration of the top/bend portion 24 of the hook 22. In certain embodiments, the receptacle 32 includes a wide opening 34 between the first side wall 38 and second side wall 40 around the upper notch 42 to allow the user/caregiver to easily find the opening 34 of the receptacle 32. Side walls 38 and 40 of the receptacle 32 then progressively get closer to each other (e.g., V-shaped sidewalls) the further the side walls extend below the upper notch 42 to help guide the hook 22 to the desired positioning within receptacle 32. At the bottom of the opening 34, the side walls 38 and 40 are preferably positioned to form a lower notch 44 dimensioned and configured for closely receiving the end of shank 26 of the hook 22. As shown, the upper notch 42 and lower notch 44 are vertically aligned to receive hook 22, though it should be understood that the particular configuration and orientation of the upper notch 42 and lower notch 44 are dependent on the dimensions of the medical device hook 22 that the receptacle 32 is intended to receive.

In certain embodiments, the top surface 37 of the rear wall 36 may slope downward from the first side wall 38 to the notch 42 and slope downward from the second side wall 40 to the notch 42. It should be understood that the downward sloping top surface 37 of the rear wall 36 also assists the user in locating the upper notch 42 with hook 22 when securing the medical device 20 to the mounting system 30. In this regard, a user can position the top portion 24 of hook 22 over the top surface 37 of the rear wall such that the hook 22 slides along the top surface 37 until it reaches upper notch 42.

According to another embodiment of the receptacle 32 (not shown), the receptacle similarly includes a rear wall 36, side wall 38, and side wall 40. However, according to this embodiment, side wall 40 is substantially vertical and forms one side of upper notch 42 and lower notch 44. In other words, as compared to the receptacle 32 as shown in the present figures, side wall 40 is substantially vertical instead of sloping downwards, and the upper notch 42 and lower notch 44 are moved such that side wall 40 forms one side of each of the notches. Thus, according to this embodiment, only side wall 38 is sloped downwards towards the lower notch 44. Similarly, the top surface 37 of the rear wall 36 may be sloped downward only from the side wall 38 to upper notch 42.

Figure 3:
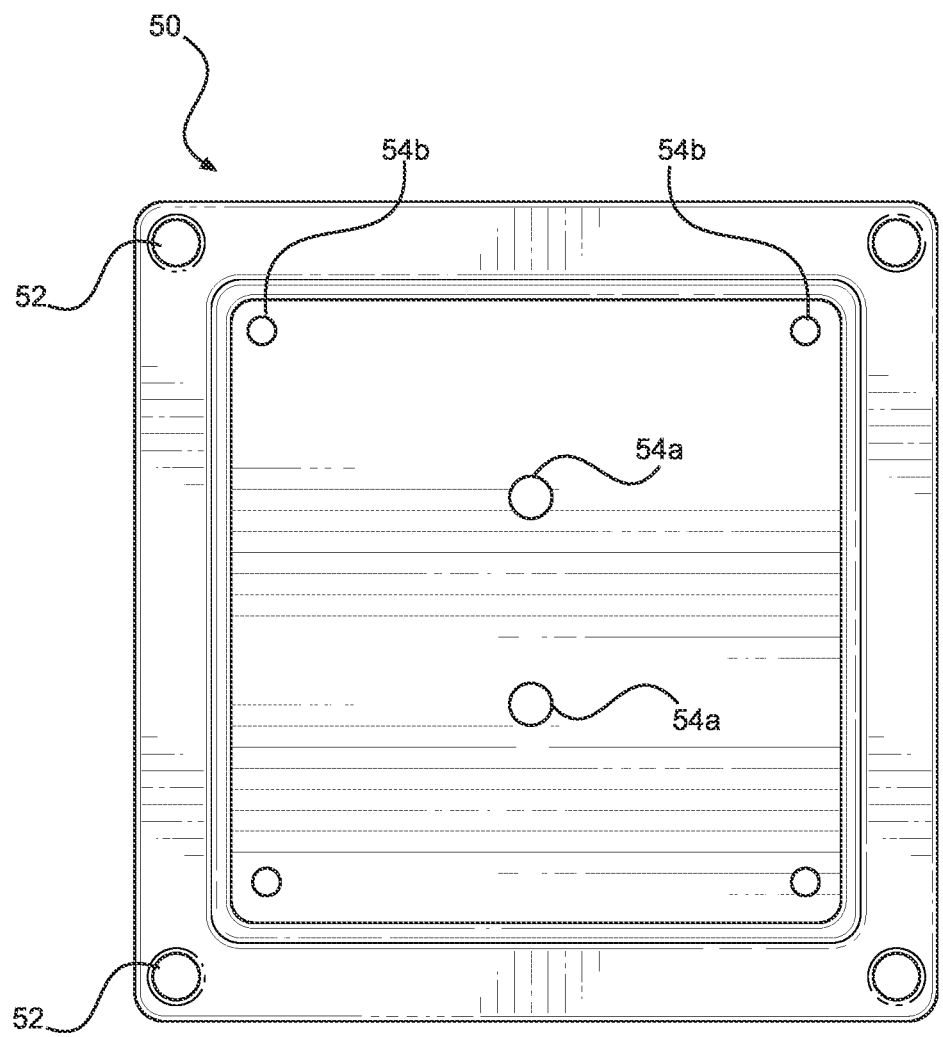
FIG. 3 depicts a front elevational view of a plate mount according to one embodiment of the disclosure.

With reference to FIGS. 2-4, the mounting system 30 further includes a plate mount 50 intended to be attached to the front of the receptacle 32 opposite rear wall 36 using screw holes 46 formed into the receptacle 32 and corresponding screw holes 52 disposed in the plate mount 50. When the plate mount 50 is attached to the receptacle 32, plate mount 50 forms a front wall of the receptacle 32. According to certain embodiments, the plate mount 50 of mounting system 30 is a standard VESA compatible plate to allow standard mounting options. According to other embodiments, plate mount 50 may be incorporated into the receptacle 32 without being a separate component.

With reference to FIG. 4, the mounting system 30 further includes an attachment component 60 that is intended to secure the mounting system 30 to the desired support structure. The attachment component 60 is intended to be secured to the plate mount 50 on the opposite side of the receptacle 32 using screw holes 54a of plate mount 50. As exemplified in the present disclosure, the attachment component 60 may be a clamp device. However, it should be understood that various other types of attachment components 60 may be used with the system of the present disclosure based on personal preference of the user, the medical device being secured by the attachment system, and/or the particular shape/configuration of the support structure in which the mounting system is intended to be secured. Further, different attachment components 60 may be used interchangeably with the same receptacle 32 and plate mount 50. For example, as depicted in FIG. 3, plate mount 50 may include different sets of screw holes 54a and 54b that are positioned in the plate mount 50 based on different attachment components intended to be secured to the particular screw hole set 54a and 54b. In other words, according to certain embodiments, the mounting system may include a "kit" of different attachment components 60 for greater compatibility options with varying support structures.

In operation, and with reference back to FIG. 1, the hook 22 of the medical device 20 is inserted into the receptacle 32 and lowered such that top/bend portion 24 of hook 22 is positioned in the upper notch 42 and the end portion 26 of hook 22 is positioned in the lower notch 44. The "V-shaped" sidewalls 36 and 38 and V-shaped top 37 of rear wall 36 of the receptacle 32 allow for greater user margin in inserting the hook 22 into the receptacle 32 while guiding the hook 22 to the upper and lower notches 42, 44 upon lowering of the of the medical device 20. Once the hook 22 is positioned within the notches 42, 44 of the receptacle 32, the sidewalls of the notches 42, 44 and weight of the device 20 together prevent any significant lateral movement of the medical device 20. According to certain embodiments, the hook 22 of the medical device 20 and receptacle 32 of the mounting system 30 are configured to restrict the motion of the device 20 while secured in the receptacle 32 to a slight rocking motion (less than about 15°) and a lifting motion (to remove the device 20 from the receptacle 32).

In preferred embodiments, the medical device 20 further includes a handle 28 positioned adjacent (e.g., directly above) the hook 22 such that the medical device 20 is able to be lifted with one hand and more easily positioned within the receptacle 32. In certain embodiments, the hook 22 and handle 28 may be combined into a unitary component that is removably secured to the medical device 20. According to other embodiments, the hook 22 is a separate component from the handle 28 such that the hook 22 is configured to be removably attached such that the hook 22 can be removed when the device 20 is not needing to be secured to a support structure. According to either of these embodiments (hook 22 and handle 28 combined into a single removable component or the hook being its own distinct removable component), an appropriate recess may be provided in the exterior surface of the medical device 20 such that a blank can replace the removed component(s) when the medical device 20 is not going to be secured to a support structure.

In preferred embodiments, the thickness of the rear wall 36 of receptacle 32 is slightly less than the space created between the hook 22 and the surface 21 of the medical device 20 that the hook 22 extends from to prevent substantial rocking of the medical device 20 while secured to the support structure.

According to certain embodiments, the hook 22 presents a low profile to allow the medical device 20 to be comfortably carried along the side of body of the person carrying the device 20. In preferred embodiments, the rear surface 21 of the medical device 20 includes a concave shape (i.e., curved inward) and the hook 22 is configured such that it does not protrude beyond the side edges of the rear surface 21 of device 20.

According to certain embodiments, the rear surface 21 of the medical device 20 is tapered and the rear wall 36 of the receptacle 32 includes a corresponding taper to ensure a better securement of the medical device 20 in the receptacle 32.

According to certain embodiments, the wider opening 34 of receptacle 12 is at least 2.5 inches. Most preferably, the opening 34 includes a width roughly the same as the handle 28 disposed above the hook 22 of the medical device 20 to help facilitate positioning of the hook 22 within the opening 34 of the receptacle 32.

Figure 5:
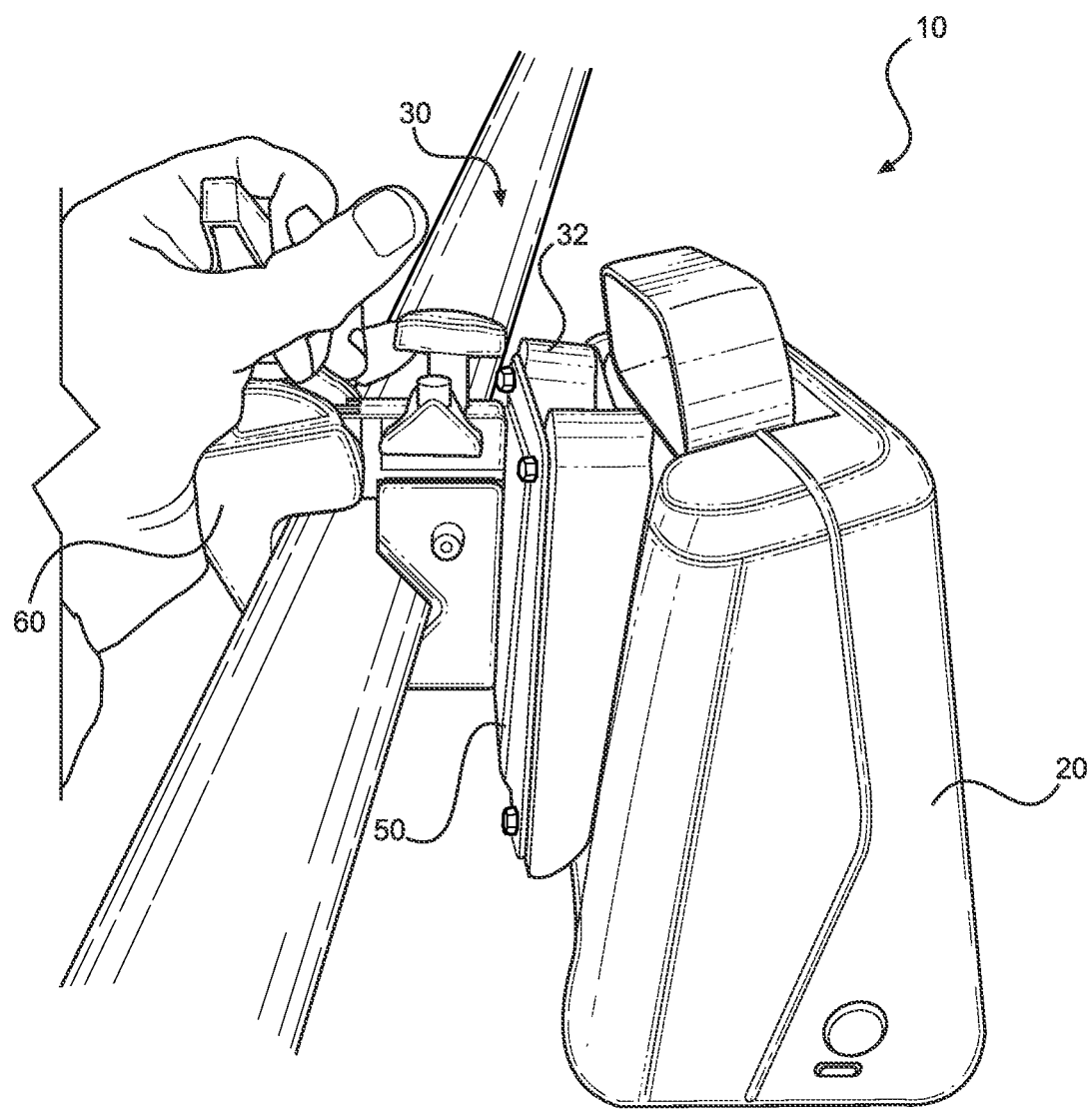
FIG. 5 depicts a side perspective view of the attachment system of FIG. 4 with the attachment component being in an orientation for securing the medical device to a horizontal pole structure according to one embodiment of the disclosure.

According to some embodiments, and with reference to FIGS. 4-5, the attachment component 60 is configured to rotate 90° with respect to the receptacle 32 to switch from a vertical configuration (see FIG. 4) for use with a vertical support structure (e.g., IV pole) to a horizontal configuration (see FIG. 5) for use with a horizontal support structure (e.g., bed rail). In certain embodiments, rotation is accomplished by unscrewing the plate mount 50 from the receptacle 32, rotating the plate mount 50 to change the orientation of the attachment component 60 as needed, and re-screwing the plate mount 50 to the receptacle 32. In other embodiments, the attachment component 60 itself may be configured to rotate with respect to a stationary plate mount 50. For example, the attachment component 60 in certain embodiments is a rotatable clamp commercially available under the trade name Manfrotto 035 Super Clamp.

According to an alternate embodiment of the disclosure, the receptacle 32 substantially as described above may be secured to the exterior surface of the medical device 20. The hook 22 may then be secured to the mounting plate 50. In other words, the system as described above is reversed with respect to the hook 22 and the receptacle 32 such that the receptacle is moved with the medical device 20 and the hook 22 is part of the mounting system 30. According to this alternate embodiment, it should be understood that the receptacle 32 would be secured to the medical device 20 such that rear wall 36 of receptacle 32 is positioned opposite the exterior surface of the medical device 20 such that upper notch 42 would be facing the hook 22 secured to the mounting system 30.

The foregoing description of preferred embodiments for this disclosure have been presented for purposes of illustration and description. They are not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A medical device attachment system comprising:
a hook including a top bend portion and a shank configured to extend down from the top bend portion of the hook;
a receptacle including a rear wall having a top surface, a first side wall, a second side wall, and an opening formed by the rear wall, the first side wall, and the second side wall, the opening including a lower notch dimensioned and configured for closely receiving an end portion of the shank of the hook, and the top surface of the rear wall including an upper notch that is vertically aligned with the lower notch and dimensioned and configured for receiving the top bend portion of the hook;
a mounting system including a plate mount having a first side and a second side and an attachment component configured to be secured to the second side of the plate mount for removably securing the mounting system to a desired support structure for the medical device,
wherein the hook is configured to be attached to an exterior surface of the medical device and the receptacle is configured to be attached to the first side of the plate mount such that the medical device is removably secured to the desired support structure when the end portion of the shank of the hook is inserted into the lower notch of the receptacle and the top bend portion of the hook is inserted into the upper notch of the receptacle.

2. The medical device attachment system of claim 1 wherein at least a portion of the top surface of the rear wall is sloped towards the upper notch.

3. The medical device attachment system of claim 1 wherein at least one of the first side wall and the second side wall include a sloped portion that is sloped towards the lower notch.

4. The medical device attachment system of claim 1 wherein the first side wall and the second side wall each include a sloped portion that is sloped towards opposing sides of the lower notch.

5. The medical device attachment system of claim 1 wherein the first side of the plate mount is configured to be removably attached to the receptacle such that the plate mount can be removed and rotated for rotating the attachment component secured to the mounting plate.

6. The medical device attachment system of claim 1 wherein, when the receptacle is attached to the first side of the plate mount, the plate mount and the receptacle are formed as a unitary component.

7. The medical device attachment system of claim 1 wherein the plate mount is configured to receive differently configured attachment components for removably securing the mounting system to differently configured support structures.

8. The medical device attachment system of claim 1 wherein the attachment component is a clamp device for removably securing the mounting system to a pole structure.

9. The medical device attachment system of claim 8 wherein the clamp device is configured to be rotated with respect to the plate mount such that the clamp device is configured to be removably secured to a vertical pole structure in a first orientation and removably secured to a horizontal pole structure in a second orientation.

10. The medical device attachment system of claim 1 wherein the mounting system is a first mounting system and the desired support structure is a first desired support structure, the medical device attachment system further comprising a second mounting system for securing to a second desired support structure such that the medical device may be moved between the first desired support structure and the second desired support structure without removing either of the first mounting system from the first desired support structure or the second mounting system from the second desired support structure.

11. The medical device attachment system of claim 1 further comprising a handle configured to be attached to the medical device.

12. The medical device attachment system of claim 1 wherein the rear wall of the receptacle includes a thickness slightly less than a depth of a space provided by the top bend portion of the hook.

13. A method for removably attaching a medical device to a support structure, the method comprising:
providing a medical device attachment system, the medical device attachment system including:
a hook including a top bend portion and a shank configured to extend down from the top bend portion of the hook,
a receptacle including a rear wall having a top surface, a first side wall, a second side wall, and an opening formed by the rear wall, the first side wall, and the second side wall, the opening including a lower notch dimensioned and configured for closely receiving an end portion of the shank of the hook, and the top surface of the rear wall including an upper notch that is vertically aligned with the lower notch and dimensioned and configured for receiving the top bend portion of the hook; and
a mounting system including a plate mount having a first side and a second side and an attachment component configured to be secured to the second side of the plate mount for removably securing the mounting system to the support structure, wherein the hook is attached to an exterior surface of the medical device and the receptacle is attached to the first side of the plate mount; and
securing the mounting system to the support structure using the attachment component;
positioning the hook adjacent the opening of the receptacle; and
positioning the shank of the hook into the opening of the receptacle such that the end portion of the shank of the hook is inserted into the lower notch and the top bend portion of the hook is inserted into the upper notch.

14. The method of claim 13 wherein at least one of the first side wall and the second side wall of the receptacle include a sloped portion that is sloped towards the lower notch, the positioning of the shank of the hook step including sliding the shank of the hook along the sloped portion until the end portion of the shank is inserted into the lower notch.

15. The method of claim 13 further comprising rotating the attachment component as compared to the receptacle based on the orientation of the support structure to which the mounting system is secured to during the securing step.

16. The method of claim 15 wherein the attachment component is a clamp device for securing the mounting system to a pole structure and wherein the orientation of the pole structure includes one of a substantially vertical orientation and a substantially horizontal orientation.

17. The method of claim 15 wherein the rotating the attachment component step includes one of rotating the plate mount with respect to the receptacle and rotating the attachment component with respect to the plate mount.

18. The method of claim 13 wherein the mounting system is a first mounting system and the support structure is a first support structure, the medical device attachment system further including a second mounting system for securing to a second support structure, the method further comprising moving the medical device between the first and second support structures without removing the first mounting system from the first support structure and without removing the second mounting system from the second support structure.

\* \* \* \* \*